United States Patent
Morrow

[11] Patent Number: 6,165,147
[45] Date of Patent: Dec. 26, 2000

[54] LOWER BACK AND HIP SUPPORT DEVICE

[76] Inventor: Kenneth Morrow, 5100 N. Tamiami Trail, Naples, Fla. 34103

[21] Appl. No.: 09/314,627

[22] Filed: May 19, 1999

[51] Int. Cl.[7] .................................................. A61F 5/00
[52] U.S. Cl. ................................. 602/19; 602/13; 602/73
[58] Field of Search ............................... 602/19, 13, 73, 602/60; 607/110, 111, 109, 112, 108, 114; 601/148, 151, 152

[56] References Cited

U.S. PATENT DOCUMENTS

| | | | |
|---|---|---|---|
| 4,621,624 | 11/1986 | Rayboy | 128/83 |
| 4,658,807 | 4/1987 | Swain | 128/78 |
| 5,407,422 | 4/1995 | Matthijs et al. | 602/19 |
| 5,503,621 | 4/1996 | Miller | 602/19 |
| 5,586,969 | 12/1996 | Yewer, Jr. | 602/19 |
| 5,620,412 | 4/1997 | Modglin | 602/24 |
| 5,628,721 | 5/1997 | Arnold et al. | 602/19 |
| 5,632,723 | 5/1997 | Grim | 602/19 |

*Primary Examiner*—Justine R. Yu
*Attorney, Agent, or Firm*—Oblon, Spivak, McClelland, Maier & Neustadt, P.C.

[57] ABSTRACT

A brace for supporting a user's lower back and hips has a front belt portion and an enlarged rear portion with a molded depression formed inside. A packet has a plurality of separately sealed liquid chambers interconnected to each other by at least one channel for allowing flow of liquid therebetween whereby equal pressure is applied to the user's lower back and hips wherever there is contact with the packet. This packet is attachable to and detachable from the molded depression so that the liquid may be replaced or cleaned by removing the plug before the packet is refilled with fresh liquid.

17 Claims, 2 Drawing Sheets

LOWER BACK AND HIP SUPPORT DEVICE

BACKGROUND OF THE INVENTION

1. Field of the Invention

This invention relates to orthopedic body braces generally and, in particular, to a lower back and hip support device.

2. Discussion of the Related Art

Lower back and hip support devices are usually sought by individuals seeking personal protection against strain and exertion encountered while lifting heavy objects or while engaging in other similar strenuous activity. Thus, the primary users of such devices are power weight lifters, construction workers and heavy industrial workers. Such devices also have medical orthopedic, chiropractic, physical therapeutic, and post-operative rehabilitative applications.

Such devices may be made of either hard plastic or tough but flexible cloth. Also, such devices may be worn either over clothing or directly against the user's skin.

A pelvic girdle made of rigid plastic is disclosed in U.S. Pat. No. 5,620,412 assigned to National Orthotic Laboratories, Inc. of Winter Haven, Fla. Flexible straps hold the various hard parts together in a so-called hip abduction system.

Another back and hip brace made of either hard plastic or hard rubber is shown in German Patent No. 1,109,315. Elastic latches are used to hold the hard sections together so that the user has some flexibility when moving.

Tough but flexible cloth pelvic belts are described in U.S. Pat. Nos. 5,407,422 and 5,586,969. Both of these belts use buckle-like closures which are adjustable and securable by Velcro®.

Another tough but flexible lower back support assembly is discussed in U.S. Pat. No. 5,628,721 which was assigned to the Royce Medical Co. of Camarillo, Calif. This prior art assembly is interesting because it has an air cushion which is inflatable or deflatable by the user. Furthermore, gel pads may be used for applying hot or cold therapeutic treatments in a narrow band conforming to the user's lower back in an orthopedically correct manner.

Nevertheless, it remains a problem in the prior art to supply a constant pressure on the lower back area and to maintain this constant pressure on the musculature and the bones from the middle lumbar vertebrae to the end of the coccyx at the bottom of the gluteus maximus.

SUMMARY OF THE INVENTION

Accordingly, one object of this invention is to provide a novel support brace capable of applying a constant pressure on the user's lower back area and of maintaining this constant pressure on the musculature and the bones from the middle lumbar vertebrae to the end of the coccyx at the bottom of the gluteus maximus through a small range of motion.

It is a secondary object of the present invention to provide a wide belt and an enlarged rear portion made of hard plastic material. A molded depression in the enlarged rear portion retains a single, large packet containing phase-change material, alkane, gel, clay, mud or another noncompressible liquid. A plurality of metal snaps or hook-and-loop strips, such as Velcro®, may be used to attach and detach the large packet, pouch or vessel of gel or liquid inside the depression of the enlarged rear portion. The large packet or pouch may have three sides closed and a fourth side opened at its top so as to enable a user to move the chemical-filled packet or pouch in and out of the rear portion for ease of recharging the chemical. Also, the wide belt may be worn without the chemical-filled packet or pouch and may still provide constant pressure through a full range of motion.

It is a tertiary object of the present invention to provide heating and cooling of the large liquid packet to a specified controlled temperature for optimum thermal contact with the muscle groups in the user's lower back and hip area for medical purposes, such as post-operative healing, prescribed physical therapy, and daily relief of lower back pain and swelling.

It is another object of the present invention to provide the large packet in the form of a plurality of separately sealed chambers interconnected by channels with one another for allowing the liquid to flow between the chambers from those under high pressure to those under less pressure so that the space between the enlarged rear portion and the clothing or skin of the user's body is filled up, thus maintaining constant pressure on all covered musculature.

It is yet another object of the present invention to form the large packet in a desired shape by heat sealing two sheets along a periphery of either polyvinyl, polyethylene, polyurethane or another similar plastic to form the packet, vacating all the air from the packet, filling the packet with the preferred liquid, and then heat sealing the packet closed.

It is a further object of the present invention to provide one or more secure plugs in the large packet to allow removal of the liquid therefrom for either replacing or cleaning before refilling the packet with fresh liquid. Thus, the brace of the present invention may be used over a very long period of time by a patient with a chronic lower back or hip problem.

It is a still further object of the present invention to provide a so-called live hinge running across the enlarged rear portion of the brace approximately two-thirds of the way from end to end. Across the live hinge, there are provided stays made of either spring steel, hard plastic or other rigid materials with excellent elastic memories for returning the brace to its original unstressed shape after pressure is removed from the user's back. Thus, as the user squats, twists to one side, or bends down, the live hinge causes the brace to maintain a constant pressure on the user's lower back and hips by creating a flow of the liquid in the large packet from the highly pressured chambers to the low pressured chambers so that any cavity existing between the user's back or the surrounding musculature and the enlarged rear portion is filled.

BRIEF DESCRIPTION OF THE DRAWINGS

A more complete appreciation of the invention and all of the attendant advantages thereof will be readily obtained as the invention becomes better understood by reference to the following detailed description when considered in connection with the accompanying drawings.

DETAILED DESCRIPTION OF THE PREFERRED EMBODIMENT

Figure 1:
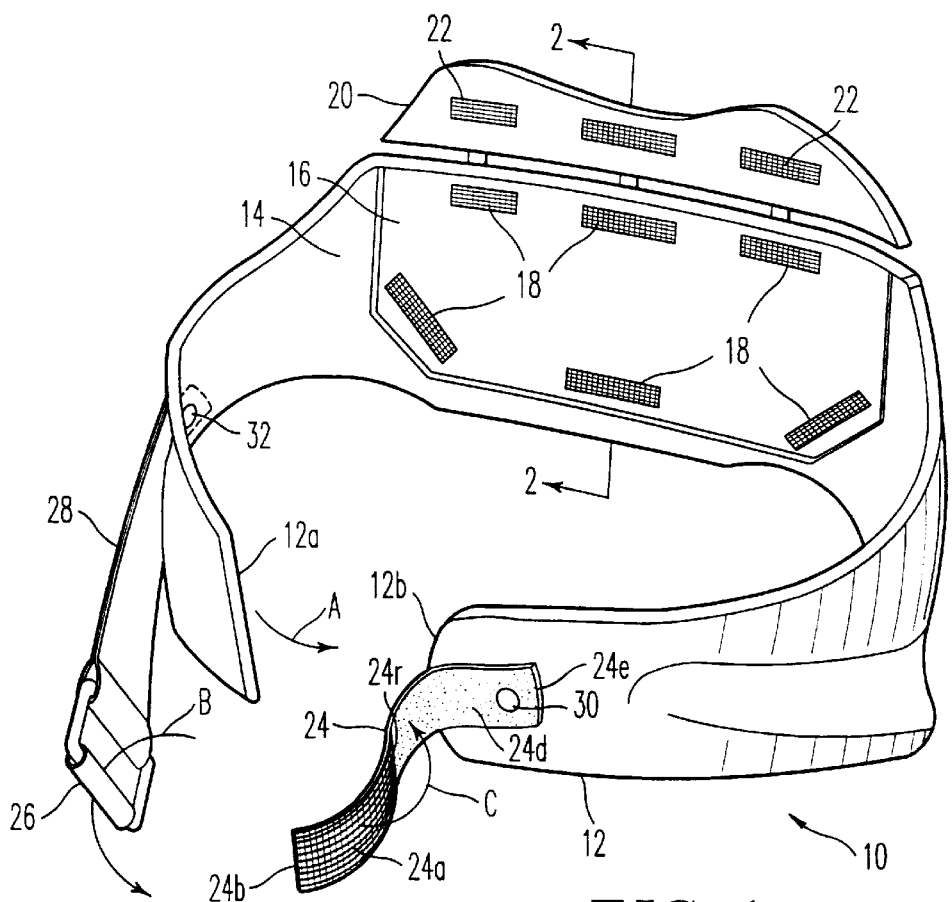
FIG. 1 shows a front perspective view of the brace of the present invention.

In FIG. 1, a perspective view of a brace 10 for supporting the lower back and hips of a user is illustrated. The brace 10 is formed out of hard, thick plastic and has a wide front belt portion 12 with an enlarged rear portion 14. A molded depression 16 is formed inside the enlarged rear portion 14 when the brace 10 is made. In the molded depression 16, there is a plurality of hook-and-loop strips 18, such as Velcro®, glued along the periphery of the molded depression 16. The enlarged rear portion 14 has mounted along its top edge an extended portion 20 which provides additional support to middle lumbar vertebrae of the user. The extended portion 20 also has a plurality of hook-and-loop strips 20 made of Velcro® and glued along an upper periphery of the extended portion 20. The wide belt portion 12 in the front of the brace 10, although made of hard, thick plastic, has some degree of flexibility so that one end 12a may be pulled in the direction of arrow A towards another end 12b. When the front belt portion 12 fits snugly against the user's stomach, the brace 10 is retained in position when the user threads a first strap 24 in the direction of arrow B through a buckle 26 at one end of a second strap 28. The first strap 24 is then folded back upon itself in the direction of arrow C to form a closed loop. One side of the first strap 24 is covered partly with hook material 24a from one end 24b to a fold line 24c. This same one side of the first strap 24 is also partly covered with loop material 24d from the fold line 24c to an opposite end 24e. A first metal rivet 30 secures the first strap 24 to the end 12b of the front belt portion 12 while a second metal rivet 32 secures the second strap 28 to the end 12a of the front belt portion 12.

Figures 2, 4:
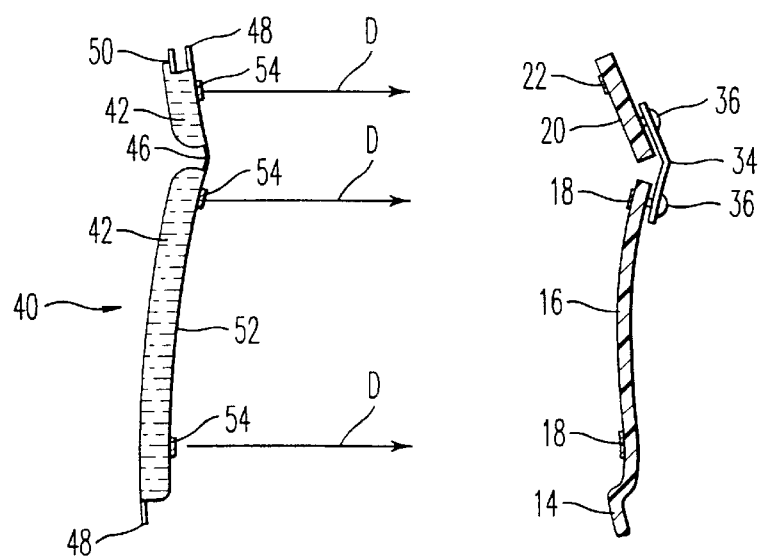
FIG. 2 shows a cross-sectional view taken along line 2—2 in FIG. 1.
FIG. 4 shows a cross-sectional view taken along line 4—4 in FIG. 3.

In FIG. 2, the enlarged rear portion 14 and the extended portion 20 are shown in cross-section. The molded depression 16 is seen to be thinner than the rest of the enlarged rear portion 14 but has the same thickness as the extended portion 20. A plurality of spring clips 34, of which only one is seen in FIG. 2, forms a so-called live hinge and connects the extended portion 20 to one side of the molded depression 16 formed in the enlarged rear portion 14. A pair of fasteners 36 secures each spring clip 34 between the extended portion 20 and the enlarged rear portion 14. One of the plurality of strips 22 of hook material is seen to be attached to a front of the extended portion 20 while two of the plurality of strips 18 of hook material are seen to be attached to a front of the molded depression 16 in the enlarged rear portion 14.

Figure 3:
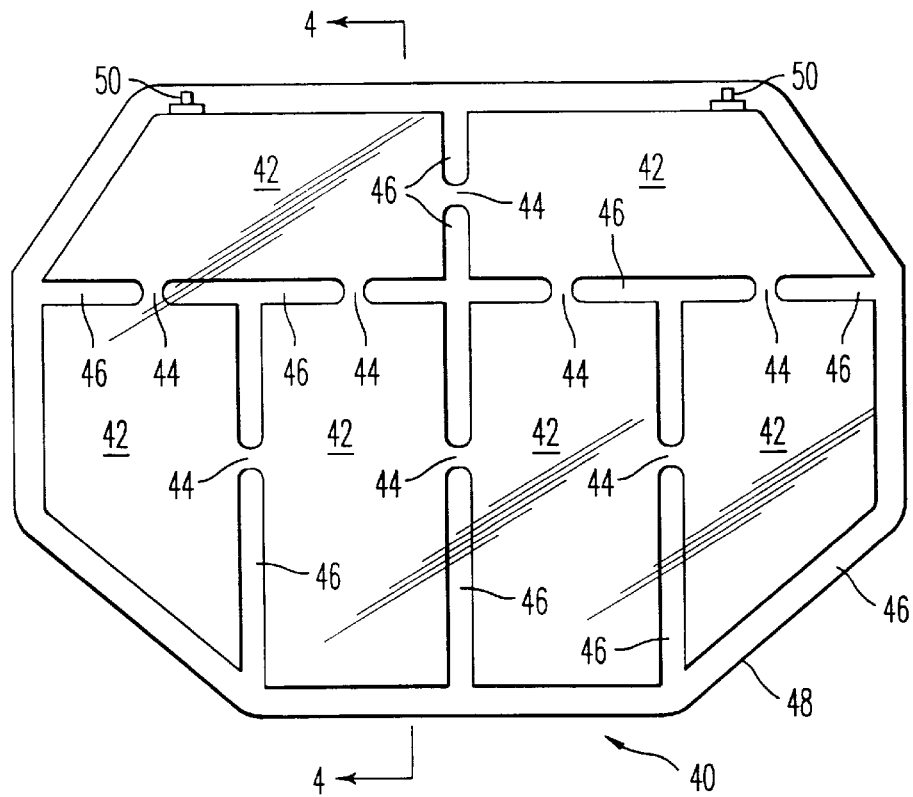
FIG. 3 shows a front plan view of the liquid packet of the present invention.

In FIG. 3, a single, large packet 40 containing gel, clay, mud or another noncompressible liquid is seen lying flat. The packet 40 has a plurality of separately sealed chambers 42 interconnected to each other by a plurality of channels 44 for allowing the flow of gel or liquid therebetween so as to apply equal pressure to the user's lower back area wherever there is contact with the packet 40. The chambers 42 are separated from each other by a plurality of heat-sealed seams 46 formed therebetween and along an outer periphery 48 of the pocket 40. One or more removable plugs 50 may be fixed into one or more of the chambers 42 so that the liquid therein may be periodically replaced or cleaned before the packet 40 is refilled with fresh liquid.

In FIG. 4, the packet 40 is shown in a cross-sectional view taken along line 4—4 in FIG. 3. Two of the sealed chambers 42 are seen to be filled with liquid and are separated from each other by one of the heat-sealed seams 46. The outer periphery 48 of the packet 40 is also illustrated. One of the removable plugs 50 is shown atop the uppermost chamber 42. On a back surface 52 of the packet 40, there is a plurality of strips 54 of hook material. These strips 54 are aligned for matching up with the strips 18 and 22 of hook material in FIG. 2 whenever the packet 40 is manually moved in the direction of arrows D for attachment to the front of the molded depression 16 and to the front of the extended portion 20 in FIG. 2. The user moves the packet 40 manually into alignment for attachment thereto either after refilling or heating or cooling the packet 40 with the liquid inside. In a similar manner, the packet 40 may be manually moved in a direction opposite to the direction of arrows D for detachment from the front of the molded depression 16 and the front of the extended portion 20 in FIG. 2.

Figure 5:
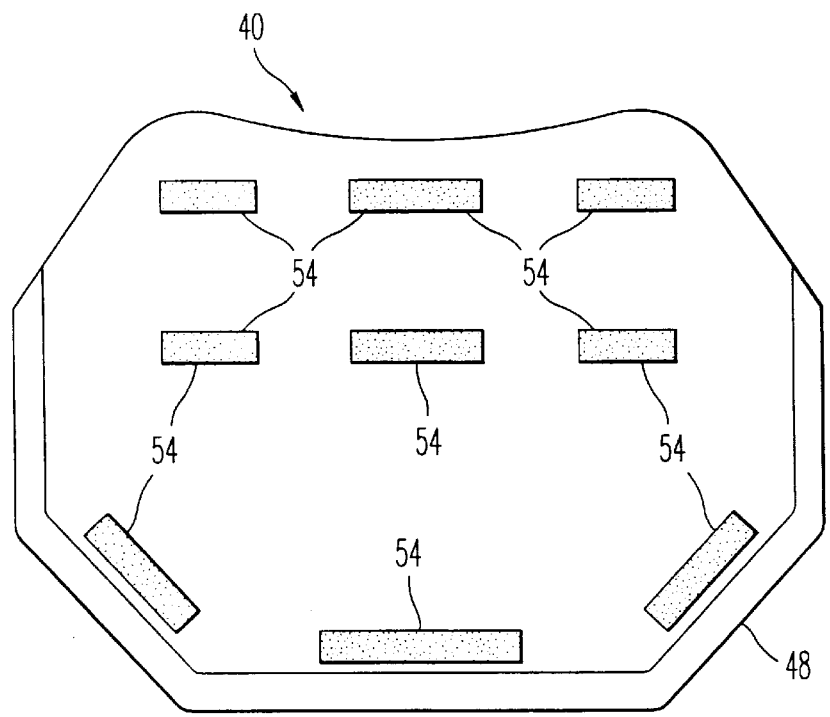
FIG. 5 shows a rear plan view of the liquid packet of the present invention.

In FIG. 5, a rear plan view of the packet 40 is seen with the plurality of strips 54 of loop material arranged around the outer periphery 48 of the packet 40. Some of the strips 54 are glued in a central portion of the packet 40.

Certainly, numerous modifications and variations of the present invention are possible in light of the above teachings. Therefore, it is to be understood that, within the scope of the appended claims, the invention may be practiced otherwise than as specifically described herein.

What is claimed as new and desired to be secured by Letters Patent of the United States is:

1. A brace for supporting a user's lower back, hips and surrounding musculature, comprising:

a front belt portion and an enlarged rear portion with a molded depression formed inside;

a packet having a plurality of liquid chambers interconnected to each other by at least one channel having liquid flow therebetween, said packet being attachable to and detachable from the molded depression; and an extended portion mounted atop the enlarged rear portion;

wherein said extended portion and the molded depression formed inside the enlarged rear portion have the same thickness;

whereby equal pressure is applied to the user's lower back, hips and surrounding musculature, wherever there is contact with the packet.

2. A brace according to claim 1, further comprising:

at least one removable plug mounted atop one of the plurality of chambers;

whereby liquid in the packet may be periodically replaced or cleaned by removing the plug before the packet is refilled with fresh liquid.

3. A brace according to claim 1, wherein:

said liquid is one of a phase-change material, an alkane, a gel, a clay, a mud and a noncompressible liquid.

4. A brace according to claim 1, further comprising:

a first strap secured to one end of the front belt portion and a second strap secured to another end of the front belt portion.

5. A brace according to claim 4, further comprising:

rivets for securing the first strap and the second strap to the front belt portion.

6. A brace according to claim 4, wherein:

said first strap has one side covered with hook material from one end to a fold line and also with loop material from the fold line to an opposite end.

7. A brace according to claim 4, wherein:

said second strap has a buckle at one end thereof.

8. A brace for supporting a user's lower back, hips and surrounding musculature, comprising:

a front belt portion and an enlarged rear portion with a molded depression formed inside;

a packet having a plurality of liquid chambers interconnected to each other by at least one channel having liquid flow therebetween, said packet being attachable to and detachable from the molded depression; and an extended portion mounted atop the enlarged rear portion;

wherein said packet is aligned for attachment to a front of the molded depression and to a front of the extended portion;

whereby equal pressure is applied to the user's lower back, hips and surrounding musculature, wherever there is contact with the packet.

9. A brace according to claim 8, further comprising:

a live hinge for mounting the extended portion along a top edge of the enlarged rear portion.

10. A brace according to claim 8, further comprising:

a plurality of strips of hook-ad-loop material secured to a back of the packet, to the front of the molded depression, and to the front of the extended portion;

whereby the packet is aligned and attached to the front of the molded depression and to the front of the extended portion.

11. A brace according to claim 9, wherein:

said live hinge includes a plurality of spring clips and a pair of fasteners for securing each spring clip between the extended portion and the enlarged rear portion.

12. A brace according to claim 8, further comprising:

at least one removable plug mounted atop one of the plurality of chambers;

whereby liquid in the packet may be periodically replaced or cleaned by removing the plug before the packet is refilled with fresh liquid.

13. A brace according to claim 8, wherein:

said liquid is one of a phase-change material, an alkane, a gel, a clay, a mud and a noncompressible liquid.

14. A brace according to claim 8, further comprising:

a first strap secured to one end of the front belt portion and a second strap secured to another end of the front belt portion.

15. A brace according to claim 14, further comprising:

rivets for securing the first strap and the second strap to the front belt portion.

16. A brace according to claim 14, wherein:

said first strap has one side covered with hook material from one end to a fold line and also with loop material from the fold line to an opposite end.

17. A brace according to claim 14, wherein:

said second strap has a buckle at one end thereof.

\* \* \* \* \*